(12) United States Patent
Carreira

(10) Patent No.: US 7,863,443 B2
(45) Date of Patent: Jan. 4, 2011

(54) PHOSPHORAMIDITE LIGAND AND PRODUCTION METHOD OF ALLYLIC AMINE USING THE SAME

(75) Inventor: Erick M. Carreira, c/o ETH Laboratory of Organic Chemistry, ETH-Hoenggerbeg, Zürich (CH)

(73) Assignees: Sumitomo Chemical Company, Limited, Tokyo (JP); Erick M. Carreira, Zurich (CH)

( * ) Notice: Subject to any disclaimer, the term of this patent is extended or adjusted under 35 U.S.C. 154(b) by 240 days.

(21) Appl. No.: 12/045,269

(22) Filed: Mar. 10, 2008

(65) Prior Publication Data

US 2009/0054689 A1 Feb. 26, 2009

(30) Foreign Application Priority Data

Aug. 22, 2007 (JP) .............................. 2007-216396

(51) Int. Cl.
*C07D 223/18* (2006.01)
(52) U.S. Cl. ..................................................... 540/587
(58) Field of Classification Search .................. 540/587
See application file for complete search history.

(56) References Cited

U.S. PATENT DOCUMENTS 6,989,461 B2 * 1/2006 Berg Van Den et al. ....... 560/40

FOREIGN PATENT DOCUMENTS

| EP | 1 364 932 A1 | 11/2003 |
|---|---|---|
| JP | 05-310659 A | 11/1993 |
| WO | WO 03/099745 A1 | 12/2003 |

OTHER PUBLICATIONS

Defieber et al., 2007, CAS: 147: 117930.*
Defieber et al., *Angew. Chem. Int. Ed.*, 46: 3139-3143 (2007).
Leitner et al., *J. Am. Chem. Soc.*, 127: 15506-15514 (2005).
Leitner et al., *Organic Letters*, 7(6): 1093-1096 (2005).
Lipowsky et al., *Chem. Commun.*, 116-117 (2004).
Polet et al., *Chem. Eur. J.*, 12: 3596-3609 (2006).
Polet et al., *Organic Letters*, 7(8): 1621-1624 (2005).
Shekhar et al., *J. Am. Chem. Soc.*, 128: 11770-11771 (2006).
Shu et al., *Angew. Chem. Int. Ed.*, 43: 4797-4800 (2004).
Takeuchi et al., *J. Am. Chem. Soc.*, 123: 9525-9534 (2001).
Takeuchi et al., *Synlett*, 12: 1954-1965 (2002).
Tissot-Croset et al., *Angew. Chem. Int. Ed.*, 43: 2426-2428 (2004).
Weihofen et al., *Chem. Commun.*, 3541-3543 (2005).
Weihofen et al., *Angew. Chem. Int. Ed.*, 45: 5546-5549 (2006).
Welter et al., *Chem. Commun.*, 896-897 (2004).
Welter et al., *Organic Letters*, 7(7): 1239-1242 (2005).
Welter et al., *Org. Biomol. Chem.*, 3: 3266-3268 (2005).
Yamashita et al., *J. Am. Chem. Soc.*, 129: 7508-7509 (2007).
Defieber et al., "Iridium-Catalyzed Synthesis of Primary Allylic Amines from Allylic Alcohols: Sulfamic Acid as Ammonia Equivalent," *Angew. Chem. Int. Ed.*, 46: 3139-3143 (published online on Mar. 12, 2007).

* cited by examiner

*Primary Examiner*—Rei-tsang Shiao
(74) *Attorney, Agent, or Firm*—Leydig, Voit & Mayer, Ltd.

(57) ABSTRACT

The present invention provides a production method of an allylic amine represented by the formula (III):

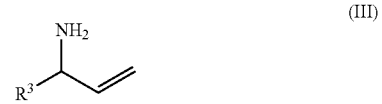

wherein $R^3$ is as defined in the specification,
which comprises reacting by an allylic alcohol represented by the formula (II):

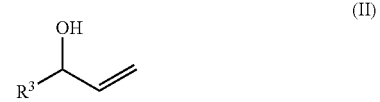

wherein $R^3$ is as defined in the specification,
with sulfamic acid, in the presence of a phosphoramidite ligand represented by the formula (I):

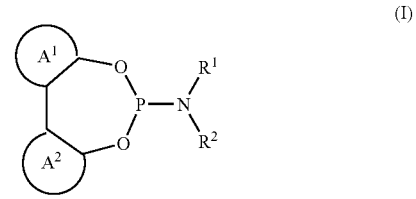

wherein each symbol is as defined in the specification, and an iridium complex. According to the present invention, a primary allylic amine can be produced directly from an allylic alcohol, without use of an activator for an allylic alcohol and conversion of an allylic alcohol into an activated compound thereof.

9 Claims, No Drawings

PHOSPHORAMIDITE LIGAND AND PRODUCTION METHOD OF ALLYLIC AMINE USING THE SAME

TECHNICAL FIELD OF THE INVENTION

The present invention relates to a novel phosphoramidite ligand, a catalyst comprising the same, and a production method of an allylic amine from an allylic alcohol using the same.

BACKGROUND OF THE INVENTION

As production methods of an allylic amine, the following documents disclose that a secondary or tertiary allylic amine is produced from an allylic carbonate using a primary or secondary amine as a nucleophilic reagent in the presence of a phosphoramidite ligand and an iridium complex:
WO03/099745;
Angew. Chem. Int. Ed. 2004.43, 4797-4800;
Org. Lett. 2005, 7, 1093-1096;
J. Am. Chem. Soc. 2005, 127, 15506-15514;
J. Am. Chem. Soc. 2006, 128, 11770-11771;
Chem. Commun. 2004, 116-117;
Chem. Commun. 2004, 896-897;
Org. Lett. 2005, 7, 1239-1242;
Chem. Commun. 2005, 3541-3543;
Org. Biomol. Chem. Commun. 2005, 3, 3266-3268;
Angew. Chem. Int. Ed. 2004, 43, 2426-2428;
Org. Lett. 2005, 7, 1621-1624;
Chem. Eur. J. 2006, 12, 3596-3609;

In addition, it is known that a primary allylic amine is produced from an allylic amide which is produced by reacting an allylic carbonate with an amide as a nucleophilic reagent in the presence of a phosphoramidite ligand and an iridium complex (Angew. Chem. Int. Ed. 2006, 45, 5546-5549). Moreover, it is known that a secondary or tertiary allylic amine is produced from an allylic alcohol using a primary or secondary amine as a nucleophilic reagent in the presence of a phosphoramidite ligand and an iridium complex (J. Am. Chem. Soc. 2007, 129, 7508-7509).

DISCLOSURE OF THE INVENTION

Since all of the above-mentioned methods use a primary or secondary amine as a nucleophilic reagent, the obtained compound is a secondary or tertiary allylic amine, which is unsuitable for the production of a primary allylic amine. Moreover, since the first and the second methods involve production from an allylic carbonate, which is an activated allylic alcohol, the methods require a step for producing an allylic carbonate from an allylic alcohol. The third method requires a Lewis acid and molecular sieves (registered trade mark) as activators for an allylic alcohol in a reaction system.

The present invention provides a method capable of direct production of a primary allylic amine from an allylic alcohol, without use of an activator for an allylic alcohol or conversion of an allylic alcohol into an activated compound thereof.

The present inventors have conducted intensive studies in an attempt to solve the aforementioned problems and found that a primary allylic amine can be produced directly from an allylic alcohol, without conventional use of an activator for an allylic alcohol or conversion of an allylic alcohol into an activated compound thereof, by reacting an allylic alcohol with sulfamic acid in the presence of a catalyst prepared from a phosphoramidite ligand represented by the following formula (I) and an iridium complex (catalyst precursor), which resulted in the completion of the present invention. Of the phosphoramidite ligands represented by the following formula (I), a phosphoramidite ligand represented by the following formula (Ia) is a novel compound.

Accordingly, the present invention provides the following.

[1] A phosphoramidite ligand represented by the formula (Ia):

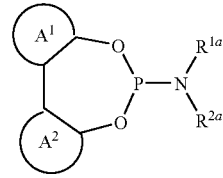

(Ia)

wherein ring $A^1$ and ring $A^2$ are the same or different and each is an aromatic hydrocarbon ring optionally having substituent(s), and $R^{1a}$ and $R^{2a}$ form, together with the nitrogen atom they are bonded to, a cyclic amino group condensed with a benzene ring, which optionally has substituent(s)

(hereinafter to be also referred to as phosphoramidite ligand (Ia)).

[2] The phosphoramidite ligand of the above-mentioned [1], wherein $R^{1a}$ and $R^{2a}$ form, together with the nitrogen atom they are bonded to,

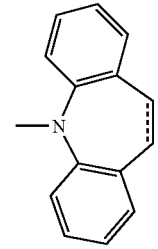

wherein

------ is a single bond or a double bond, which optionally has substituent(s).

[3] The phosphoramidite ligand of the above-mentioned [1], wherein $R^{1a}$ and $R^{2a}$ form, together with the nitrogen atom they are bonded to,

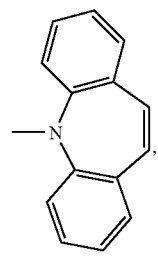

which optionally has substituent(s).

[4] The phosphoramidite ligand of the above-mentioned [1], wherein ring $A^1$ and ring $A^2$ are the same or different and each is a benzene ring optionally having substituent(s) or a naphthalene ring optionally having substituent(s).

[5] The phosphoramidite ligand of the above-mentioned [1], wherein ring $A^1$ and ring $A^2$ are both benzene rings optionally having substituent(s) or both naphthalene rings optionally having substituent(s).

[6] The phosphoramidite ligand of the above-mentioned [1], which is

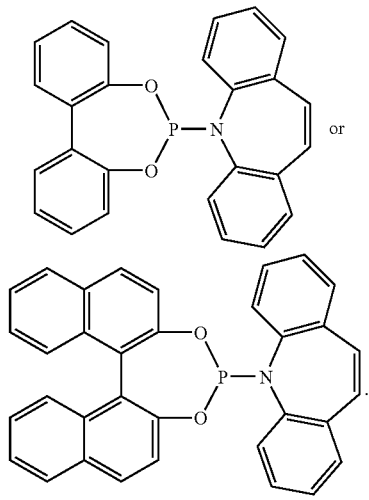

or

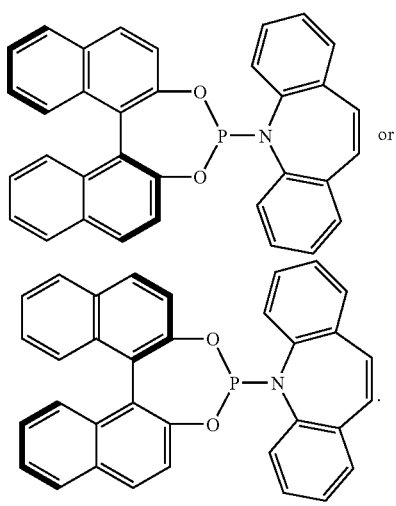

[7] The phosphoramidite ligand of the above-mentioned [1], which is a chiral ligand.

[8] The phosphoramidite ligand of the above-mentioned [1], which is

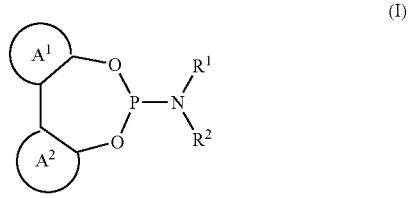

[9] A catalyst prepared from the phosphoramidite ligand of any of the above-mentioned [1] to [8] and an iridium complex.

[10] The catalyst of the above-mentioned [9], wherein the iridium complex is $\{Ir(1,5\text{-cyclooctadiene})Cl\}_2$ or $\{IrCl(cyclooctene)_2\}_2$.

[11] A production method of an allylic amine represented by the formula (III):

 (III)

wherein $R^3$ is an alkyl group optionally having substituent(s), an alkenyl group optionally having substituent(s), a cycloalkyl group optionally having substituent(s), an aryl group optionally having substituent(s) or an aralkyl group optionally having substituent(s)

(hereinafter to be also referred to as allylic amine (III)), which comprises reacting an allylic alcohol represented by the formula (II):

 (II)

wherein $R^3$ is as defined above (hereinafter to be also referred to as allylic alcohol (II)), with sulfamic acid, in the presence of a phosphoramidite ligand represented by the formula (I):

(I)

wherein ring $A^1$ and ring $A^2$ are the same or different and each is an aromatic hydrocarbon ring optionally having substituent(s), and $R^1$ and $R^2$ are the same or different and each is an alkyl group optionally having substituent(s), an aryl group optionally having substituent(s) or an aralkyl group optionally having substituent(s), or $R^1$ and $R^2$ form, together with the nitrogen atom they are bonded to, a cyclic amino group optionally having substituent(s) (hereinafter to be also referred to as phosphoramidite ligand (I)), and an iridium complex.

[12] The production method of the above-mentioned [11], wherein the reaction is carried out in a solvent comprising N,N-dimethylformamide.

[13] The production method of the above-mentioned [11], wherein $R^1$ and $R^2$ form, together with the nitrogen atom they are bonded to, a cyclic amino group optionally having substituent(s).

[14] The production method of the above-mentioned [11], wherein the phosphoramidite ligand represented by the formula (I) is the phosphoramidite ligand of any of the above-mentioned [1] to [8].

[15] The production method of the above-mentioned [11], wherein the iridium complex is $\{Ir(1,5\text{-cyclooctadiene})Cl\}_2$ or $\{IrCl(cyclooctene)_2\}_2$.

According to the present invention, an allylic alcohol can be directly subjected to an amination reaction without conventional activation thereof. In addition, since sulfamic acid, rather than a primary or secondary amine, is reacted, a primary allylic amine can be obtained.

The present invention is explained in detail in the following.

Ring $A^1$ and ring $A^2$ are the same or different and each is an aromatic hydrocarbon ring optionally having substituent(s).

Examples of the "aromatic hydrocarbon ring" of the "aromatic hydrocarbon ring optionally having substituent(s)" for ring $A^1$ or ring $A^2$ include a $C_{6-14}$ aromatic hydrocarbon ring such as a benzene ring, a naphthalene ring, an anthracene ring, a phenanthrene ring and the like. Of these, a $C_{6-12}$ aromatic hydrocarbon ring is preferable, and a benzene ring and a naphthalene ring are particularly preferable. The aromatic hydrocarbon ring is optionally condensed with an alicyclic hydrocarbon such as a $C_{3-6}$ cycloalkane (e.g., cyclohexane, cyclopentane etc.), a $C_{3-6}$ cycloalkene (e.g., cyclohexene, cyclopentene etc.) and the like. The aromatic hydrocarbon ring optionally has substituent(s) at substitutable position(s). Examples of the substituent include a halogen atom, a $C_{1-6}$ alkyl group (e.g., methyl, ethyl, propyl, isopropyl etc.), a $C_{2-6}$ alkenyl group (e.g., vinyl, allyl etc.), a $C_{1-6}$ alkoxy group (e.g., methoxy, ethoxy, propoxy, isopropoxy etc.), a $C_{1-6}$ haloalkyl group (e.g., fluoromethyl, difluoromethyl, trifluoromethyl, 2-fluoroethyl etc.), a $C_{1-6}$ haloalkoxy group (e.g., fluoromethoxy, difluoromethoxy, trifluoromethoxy, 2-fluoroethoxy etc.), a tri-$C_{1-6}$ alkylsilyl group (e.g., trimethylsilyl, triethylsilyl etc.), a $C_{6-10}$ aryl group (e.g., phenyl, naphthyl etc.), a $C_{7-10}$ aralkyl group (e.g., benzyl, phenethyl etc.), a $C_{6-10}$ aryloxy group (e.g., phenoxy, naphthyloxy etc.), a $C_{7-10}$ aralkyloxy group (e.g., benzyloxy, phenethyloxy etc.), a nitro group, a cyano group, a $C_{1-6}$ alkyl-carbonyl group (e.g., acetyl, propanoyl etc.), a $C_{1-6}$ alkoxy-carbonyl group (e.g., methoxycarbonyl, ethoxycarbonyl, butoxycarbonyl etc.) and the like. The above-mentioned $C_{1-6}$ alkyl group and $C_{2-6}$ alkenyl group exemplified as the substituent are optionally substituted by a $C_{1-6}$ alkyl-carbonyl group, a $C_{1-6}$ alkoxy-carbonyl group or the like. The above-mentioned $C_{6-10}$ aryl group, $C_{7-10}$ aralkyl group, $C_{6-10}$ aryloxy group and $C_{7-10}$ aralkyloxy group exemplified as the substituent are optionally substituted by a halogen atom, a $C_{1-6}$ alkyl group, a $C_{2-6}$ alkenyl group, a $C_{1-6}$ alkoxy group, a $C_{1-6}$ haloalkyl group, a $C_{1-6}$ haloalkoxy group or the like. The number of the substituents is not particularly limited, but preferably 0 to 3. The substituents may be the same or different.

It is preferred that ring $A^1$ and ring $A^2$ are the same or different and each is a $C_{6-12}$ aromatic hydrocarbon ring optionally having substituent(s), and it is more preferred that ring $A^1$ and ring $A^2$ are the same or different and each is a benzene ring optionally having substituent(s) or a naphthalene ring optionally having substituent(s) (preferably both benzene rings optionally having substituent(s) or both naphthalene rings optionally having substituent(s)). It is particularly preferred that ring $A^1$ and ring $A^2$ are the same or different and each is a benzene ring or a naphthalene ring (preferably both benzene rings or both naphthalene rings).

$R^1$ and $R^2$ are the same or different and each is an alkyl group optionally having substituent(s), an aryl group optionally having substituent(s) or an aralkyl group optionally having substituent(s), or $R^1$ and $R^2$ form, together with the nitrogen atom they are bonded to, a cyclic amino group optionally having substituent(s).

Examples of the "alkyl group" of the "alkyl group optionally having substituent(s)" for $R^1$ or $R^2$ include a linear or branched $C_{1-10}$ alkyl group such as methyl, ethyl, propyl, isopropyl, butyl, isobutyl, sec-butyl, tert-butyl, pentyl, isopentyl, neopentyl, hexyl, heptyl, octyl, nonyl, decyl and the like. Of these, a $C_{1-6}$ alkyl group is preferable. The alkyl group optionally has substituent(s) at substitutable position(s). Examples of the substituent include a halogen atom, a $C_{1-6}$ alkyl group (e.g., methyl, ethyl, propyl, isopropyl etc.), a $C_{2-6}$ alkenyl group (e.g., vinyl, allyl etc.), a $C_{1-6}$ alkoxy group (e.g., methoxy, ethoxy, propoxy, isopropoxy etc.), a $C_{1-6}$ haloalkyl group (e.g., fluoromethyl, difluoromethyl, trifluoromethyl, 2-fluoroethyl etc.), a $C_{1-6}$ haloalkoxy group (e.g., fluoromethoxy, difluoromethoxy, trifluoromethoxy, 2-fluoroethoxy etc.), a tri-$C_{1-6}$ alkylsilyl group (e.g., trimethylsilyl, triethylsilyl etc.), a $C_{6-10}$ aryl group (e.g., phenyl, naphthyl etc.), a $C_{7-10}$ aralkyl group (e.g., benzyl, phenethyl etc.), a $C_{6-10}$ aryloxy group (e.g., phenoxy, naphthyloxy etc.), a $C_{7-10}$ aralkyloxy group (e.g., benzyloxy, phenethyloxy etc.), a nitro group, a cyano group, a $C_{1-6}$ alkyl-carbonyl group (e.g., acetyl, propanoyl etc.), a $C_{1-6}$ alkoxy-carbonyl group (e.g., methoxycarbonyl, ethoxycarbonyl, butoxycarbonyl etc.) and the like. The above-mentioned $C_{6-10}$ aryl group, $C_{7-10}$ aralkyl group, $C_{6-10}$ aryloxy group and $C_{7-10}$ aralkyloxy group exemplified as the substituent are optionally substituted by a halogen atom, a $C_{1-6}$ alkyl group (e.g., methyl, ethyl, propyl, isopropyl etc.), a $C_{2-6}$ alkenyl group (e.g., vinyl, allyl etc.), a $C_{1-6}$ alkoxy group, a $C_{1-6}$ haloalkyl group, a $C_{1-6}$ haloalkoxy group or the like. The number of the substituents is not particularly limited, but preferably 0 to 5. The substituents may be the same or different.

The "alkyl group optionally having substituent(s)" is preferably a $C_{1-10}$ alkyl group, more preferably a $C_{1-6}$ alkyl group, particularly preferably methyl, ethyl, propyl or isopropyl.

Examples of the "aryl group" of the "aryl group optionally having substituent(s)" for $R^1$ or $R^2$ include a $C_{6-14}$ aryl group such as phenyl, naphthyl, anthryl, phenanthryl, acenaphthyl, biphenylyl and the like. Of these, a $C_{6-10}$ aryl group is preferable, and phenyl is particularly preferable. The aryl group optionally has substituent(s) at substitutable position(s). Examples of the substituent include those similar to the substituent of the "aromatic hydrocarbon ring optionally having substituent(s)" for ring $A^1$ or ring $A^2$. The number of the substituents is not particularly limited, but preferably 0 to 3. The substituents may be the same or different.

The "aryl group optionally having substituent(s)" is preferably a $C_{6-14}$ aryl group, more preferably a $C_{6-10}$ aryl group, particularly preferably phenyl.

With regards to the "aralkyl group" of the "aralkyl group optionally having substituent(s)" for $R^1$ or $R^2$, examples of the alkyl moiety include those similar to the "alkyl group" of the above-mentioned "alkyl group optionally having substituent(s)", and examples of the aryl moiety include those similar to the "aryl group" of the above-mentioned "aryl group optionally having substituent(s)". Specific examples thereof include a $C_{7-13}$ aralkyl group such as benzyl, phenethyl, 1-phenylethyl, 1-, 2- or 3-phenylpropyl, 1- or 2-naphthylmethyl, 1- or 2-(1-naphthyl)ethyl, 1- or 2-(2-naphthyl)ethyl and the like. Of these, a $C_{7-10}$ aralkyl group is preferable. The aralkyl group optionally has substituent(s) at substitutable position(s). Examples of the substituent include those similar to the substituent of the "aromatic hydrocarbon ring optionally having substituent(s)" for ring $A^1$ or ring $A^2$. The number of the substituents is not particularly limited, but preferably 0 to 5. The substituents may be the same or different.

The "aralkyl group optionally having substituent(s)" is preferably a $C_{7-13}$ aralkyl group, more preferably a $C_{7-10}$ aralkyl group, particularly preferably benzyl or 1-phenylethyl.

Examples of the "cyclic amino group" of the "cyclic amino group optionally having substituent(s)" formed by $R^1$ and $R^2$ together with the nitrogen atom they are bonded to include a 3- to 10-membered cyclic amino group such as aziridin-1-yl, azetidin-1-yl, pyrrolidin-1-yl, piperidino, azepin-1-yl, azepan-1-yl and the like. Of these, a 3- to 8-membered cyclic amino group is preferable. The cyclic amino group is optionally condensed with a benzene ring. The cyclic amino group optionally has substituent(s) at substitutable position(s). Examples of the substituent include those similar to the substituent of the "aromatic hydrocarbon ring optionally having substituent(s)" for ring $A^1$ or ring $A^2$. The number of the substituents is not particularly limited, but preferably 0 to 5. The substituents may be the same or different.

The "cyclic amino group optionally having substituent(s)" is preferably a 3- to 8-membered cyclic amino group optionally condensed with a benzene ring, which optionally has substituent(s);

more preferably a 3- to 8-membered cyclic amino group condensed with a benzene ring, which optionally has substituent(s);

further more preferably

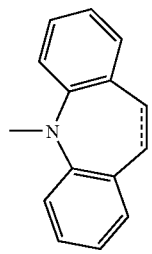

wherein

‑‑‑‑‑‑ is a single bond or a double bond, which optionally has substituent(s) (preferably has no substituent);

particularly preferably

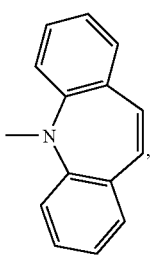

which optionally has substituent(s) (preferably having no substituent).

$R^1$ and $R^2$ preferably form, together with the nitrogen atom they are bonded to, a cyclic amino group optionally having substituent(s);

more preferably form, together with the nitrogen atom they are bonded to, a 3- to 10-membered cyclic amino group (preferably a 3- to 8-membered cyclic amino group) optionally condensed with a benzene ring, which optionally has substituent(s); further more preferably form, together with the nitrogen atom they are bonded to, a 3- to 10-membered cyclic amino group (preferably a 3- to 8-membered cyclic amino group) condensed with a benzene ring, which optionally has substituent(s); still more preferably

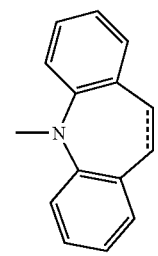

wherein

‑‑‑‑‑‑ is a single bond or a double bond, which optionally has substituent(s) (preferably has no substituent);

particularly preferably

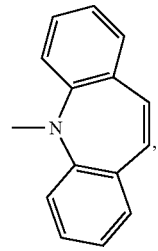

which optionally has substituent(s) (preferably has no substituent).

Examples of the "cyclic amino group" of the "cyclic amino group condensed with a benzene ring, which optionally has substituent(s)" formed by $R^{1a}$ and $R^{2a}$ together with the nitrogen atom they are bonded to include those similar to the "cyclic amino group" of the "cyclic amino group optionally having substituent(s)" formed by $R^1$ and $R^2$ together with the nitrogen atom they are bonded to.

$R^{1a}$ and $R^{2a}$ preferably form, together with the nitrogen atom they are bonded to, a 3- to 10-membered cyclic amino group (preferably a 3- to 8-membered cyclic amino group) condensed with a benzene ring, which optionally has substituent(s);

more preferably

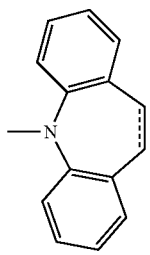

wherein

====== is a single bond or a double bond, which optionally has substituent(s) (preferably has no substituent);

particularly preferably

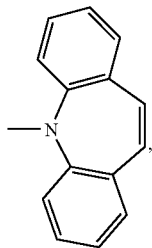

which optionally has substituent(s) (preferably has no substituent).

$R^3$ is an alkyl group optionally having substituent(s), an alkenyl group optionally having substituent(s), a cycloalkyl group optionally having substituent(s), an aryl group optionally having substituent(s) or an aralkyl group optionally having substituent(s).

Examples of the "alkyl group optionally having substituent(s)" for $R^3$ include those similar to the "alkyl group optionally having substituent(s)" for $R^1$ or $R^2$.

The "alkyl group optionally having substituent(s)" is preferably a $C_{1-10}$ alkyl group optionally having $C_{7-10}$ aralkyloxy group(s), more preferably a $C_{1-6}$ alkyl group optionally having $C_{7-10}$ aralkyloxy group(s), particularly preferably benzyloxymethyl.

Examples of the "alkenyl group" of the "alkenyl group optionally having substituent(s)" for $R^3$ include a linear or branched $C_{2-10}$ alkenyl group such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Of these, a $C_{2-6}$ alkenyl group is preferable. The alkenyl group has substituent(s) at substitutable position(s). Examples of the substituent include those similar to the substituent of the "alkyl group optionally having substituent(s)" for $R^1$ or $R^2$. The number of the substituents is not particularly limited, but preferably 0 to 5. The substituents may be the same or different.

The "alkenyl group optionally having substituent(s)" is preferably a $C_{2-10}$ alkenyl group, more preferably a $C_{2-6}$ alkenyl group, particularly preferably allyl.

Examples of the "cycloalkyl group" of the "cycloalkyl group optionally having substituent(s)" for $R^3$ include a $C_{3-10}$ cycloalkyl group such as cyclopropyl, cyclobutyl, cyclopentyl, cyclohexyl, cycloheptyl, cyclooctyl and the like. Of these, a $C_{3-6}$ cycloalkyl group is preferable. The cycloalkyl group has substituent(s) at substitutable position(s). Examples of the substituent include those similar to the substituent of the "aromatic hydrocarbon ring optionally having substituent(s)" for ring $A^1$ or ring $A^2$. The number of the substituents is not particularly limited, but preferably 0 to 3. The substituents may be the same or different.

The "cycloalkyl group optionally having substituent(s)" is preferably a $C_{3-10}$ cycloalkyl group, more preferably a $C_{3-6}$ cycloalkyl group, particularly preferably cyclohexyl.

Examples of the "aryl group optionally having substituent(s)" for $R^3$ include those similar to the "aryl group optionally having substituent(s)" for $R^1$ or $R^2$.

The "aryl group optionally having substituent(s)" is preferably a $C_{6-14}$ aryl group, more preferably a $C_{6-10}$ aryl group, particularly preferably phenyl.

Examples of the "aralkyl group optionally having substituent(s)" for $R^3$ include those similar to the "aralkyl group optionally having substituent(s)" for $R^1$ or $R^2$.

The "aralkyl group optionally having substituent(s)" is preferably a $C_{7-13}$ aralkyl group, more preferably a $C_{7-10}$ aralkyl group, particularly preferably phenethyl.

In the present invention, allylic amine (III) can be produced by reacting allylic alcohol (II) with sulfamic acid in the presence of phosphoramidite ligand (I) and an iridium complex (catalyst precursor). The complex prepared from phosphoramidite ligand (I) and an iridium complex (catalyst precursor) is used as a catalyst for the above-mentioned reaction.

Examples of phosphoramidite ligand (I) used in the present invention include the following ligands. Phosphoramidite ligand (I) may be a chiral ligand, and chiral allylic amine (III) can be produced using a chiral ligand.

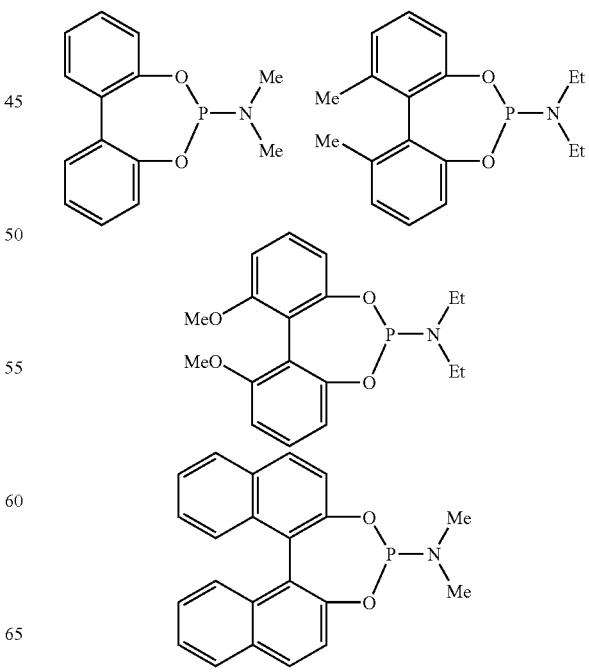

-continued
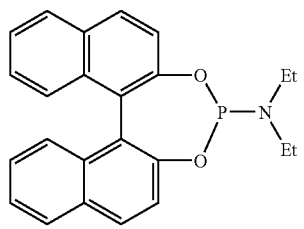
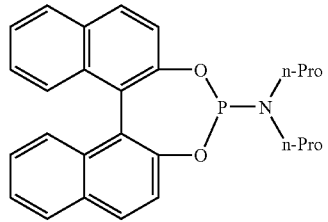
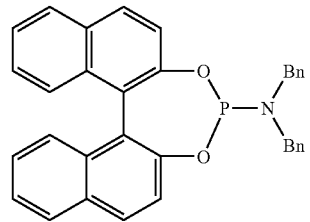
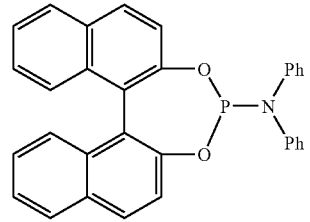
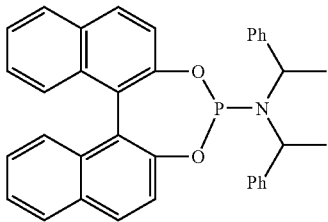
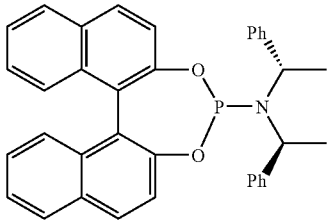
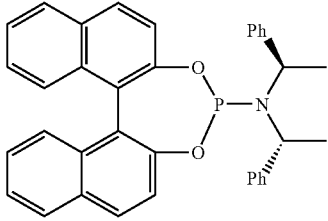
-continued
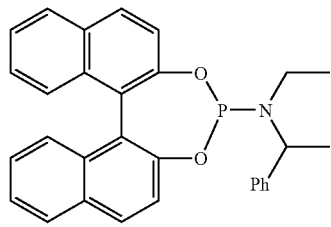
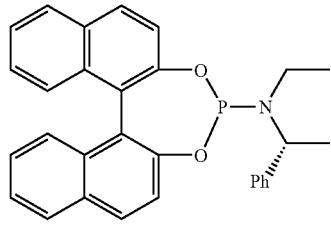
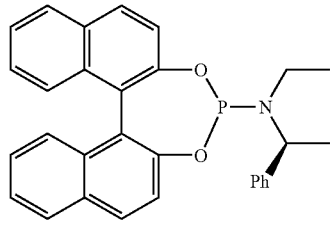
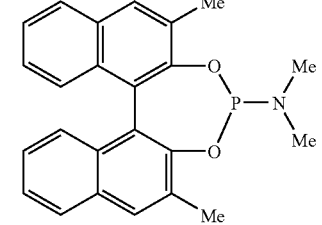
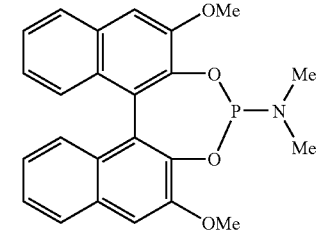
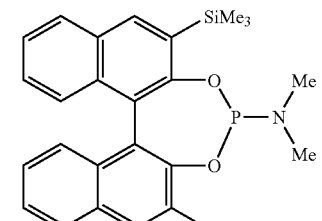
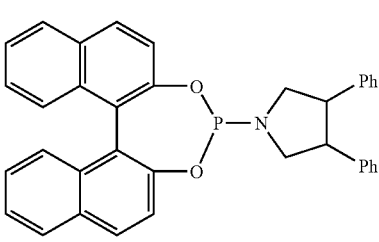

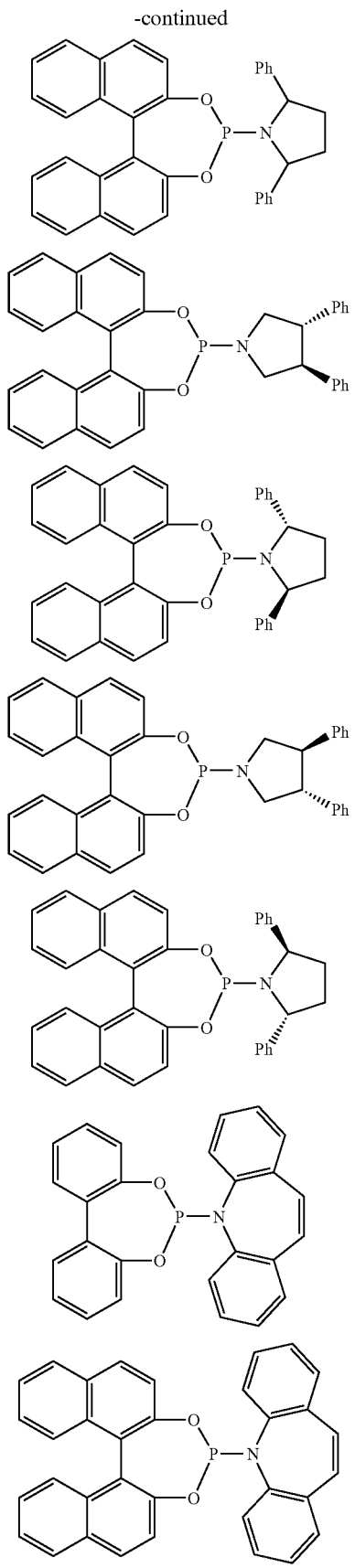
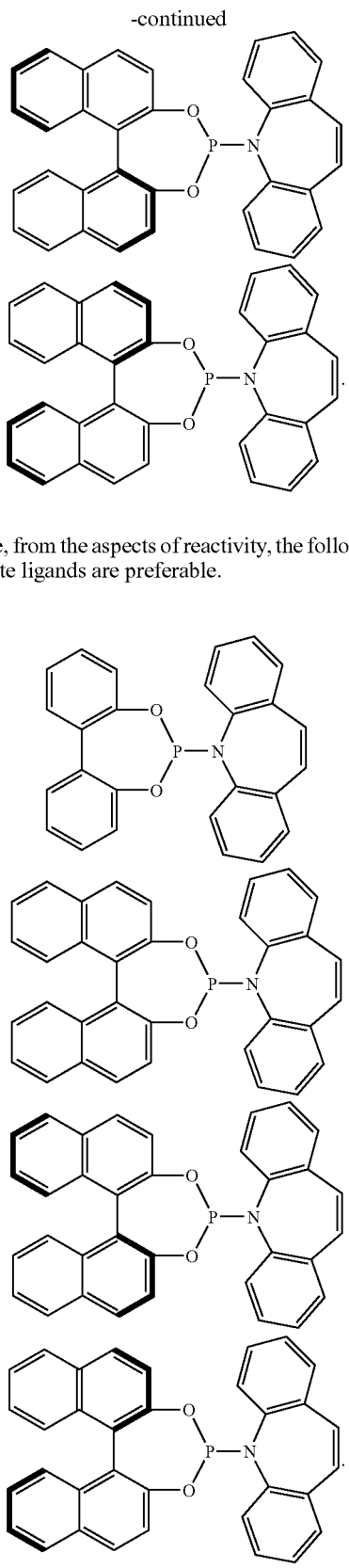
Of these, from the aspects of reactivity, the following phosphoramidite ligands are preferable.
The iridium complex may be commercially available, and examples thereof include {Ir(1,5-cyclooctadiene)Cl}$_2$ (hereinafter 1,5-cyclooctadiene is to be abbreviated as "cod"), {IrCl(cyclooctene)$_2$}$_2$ (hereinafter cyclooctene is to be abbreviated as "coe"), Ir(acetylacetonate) (CO)$_2$ (hereinafter acetylacetonate is to be abbreviated as "acac"), {Ir(cod)$_2$}BF$_4$, {Ir(cod)$_2$}PF$_6$, {Ir(cod)$_2$}ClO$_4$, {Ir(cod)$_2$}SbF$_6$, {Ir(cod)$_2$}CF$_3$SO$_3$, {Ir(cod)$_2$}B(C$_6$F$_5$)$_4$ and the like. Of these, from the aspects of reactivity, {Ir(cod)Cl}$_2$, {IrCl(coe)$_2$}$_2$ and the like are preferable, and {Ir(cod)Cl}$_2$ and {IrCl(coe)$_2$}$_2$ are particularly preferable.

Preferable Examples of the combination of phosphoramidite ligand (I) and an iridium complex include a combination of phosphoramidite ligand (I) selected from

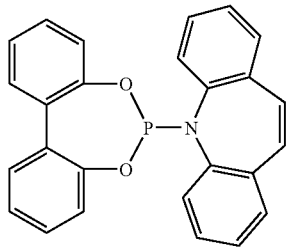

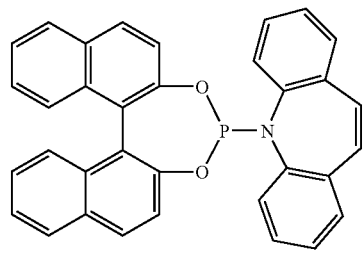

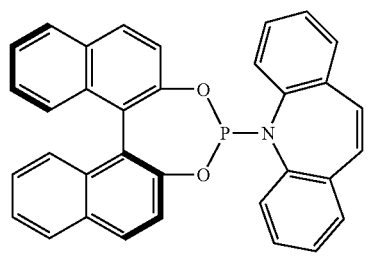

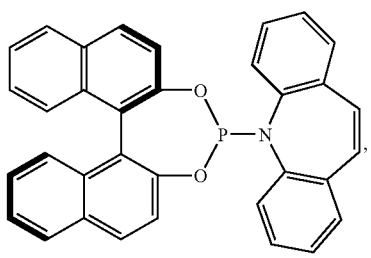

and an iridium complex selected from {Ir(cod)Cl}$_2$ and {IrCl(coe)$_2$}$_2$.

The complex of phosphoramidite ligand (I) and an iridium complex (catalyst precursor) is easily prepared in the reaction system. For example, it can be prepared by mixing phosphoramidite ligand (I) with an iridium complex in a solvent.

The amount of phosphoramidite ligand (I) to be used varies depending on the kind of the iridium complex to be used. For example, when the iridium complex is {Ir(cod)Cl}$_2$, it is generally 1 to 3 mol, preferably 1.5 to 2.5 mol, per 1 mol of the iridium complex, and when the iridium complex is {IrCl(coe)$_2$}$_2$, it is generally 1 to 3 mol, preferably 1.5 to 2.5 mol, per 1 mol of the iridium complex.

In addition, the amount of phosphoramidite ligand (I) to be used is generally 0.01 to 0.2 mol, preferably 0.02 to 0.1 mol, per 1 mol of allylic alcohol (II).

The above-mentioned solvent is preferably the same as the solvent used for the reaction of allylic alcohol (II) with sulfamic acid. Of these, from the aspects of reactivity, a solvent containing N,N-dimethylformamide is preferable. Examples thereof include N,N-dimethylformamide alone; a mixed solvent containing N,N-dimethylformamide and a dipolar aprotonic solvent other than N,N-dimethylformamide (e.g., N,N-dimethylacetamide, dimethyl sulfoxide etc.), and the like. In the present invention, the reaction is preferably carried out in a dipolar aprotonic solvent alone, that is, N,N-dimethylformamide alone or a mixed solvent containing N,N-dimethylformamide and a dipolar aprotonic solvent other than N,N-dimethylformamide (e.g., N,N-dimethylacetamide, dimethyl sulfoxide etc.).

The amount of sulfamic acid to be used is generally 1 to 4 mol, preferably 1 to 2 mol, per 1 mol of allylic alcohol (II), from the aspects of reactivity.

In the present invention, the reaction is carried out as follows.

First, a complex is prepared by mixing phosphoramidite ligand (I) with an iridium complex in a solvent.

Then, allylic alcohol (II) and sulfamic acid are added to the mixture. While the order of addition of these is not particularly limited, sulfamic acid is preferably added after addition of allylic alcohol (II). They may be added after being dissolved or suspended in a solvent, or added dropwise.

The reaction temperature is generally 0 to 80° C., preferably 20 to 60° C., and the reaction time varies depending on the kinds of phosphoramidite ligand (I) and allylic alcohol (II), and it is generally 1 to 24 hr, preferably 2 to 10 hr.

After completion of the reaction, allylic amine (III) is obtained by conventional workup such as separating operation, concentration and the like. Where necessary, it may be purified by an operation such as recrystallization, column chromatography and the like. After completion of the reaction or after conventional workup, moreover, an operation such as a treatment with an acid such as hydrochloric acid and the like, introduction of an amino-protecting group (e.g., tert-butoxycarbonyl group (Boc group), benzoyl group (Bz group), trifluoroacetyl group etc.), and the like may be successively performed, thereby to convert allylic amine (III) into a salt thereof or a derivative thereof. In this way, isolation may be facilitated, or the stability of allylic amine (III) may be improved.

In the present invention, use of chiral phosphoramidite ligand (I) affords chiral allylic amine (IIIa) (the carbon atom which the amino group is bonded to is a chiral center) from racemic allylic alcohol (II), as shown below. The steric configuration of chiral allylic amine (III) is determined depending on the steric configuration of chiral phosphoramidite ligand (I). For example, when chiral phosphoramidite ligand (I) is

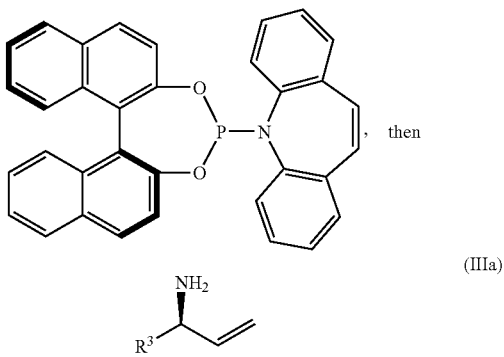

(IIIa)

is obtained, and when chiral phosphoramidite ligand (I) is

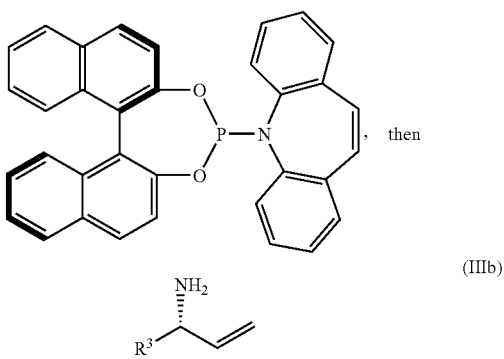

(IIIb)

is obtained.

Of phosphoramidite ligand (I), phosphoramidite ligand (Ia) is novel, and can be produced, for example, according to the following method, that is, by (Step 1) reacting diol (IVa) with phosphorus trichloride to give phosphorcholoridite (Va), and then (Step 2) reacting phosphorcholoridite (Va) with amine (VIa).

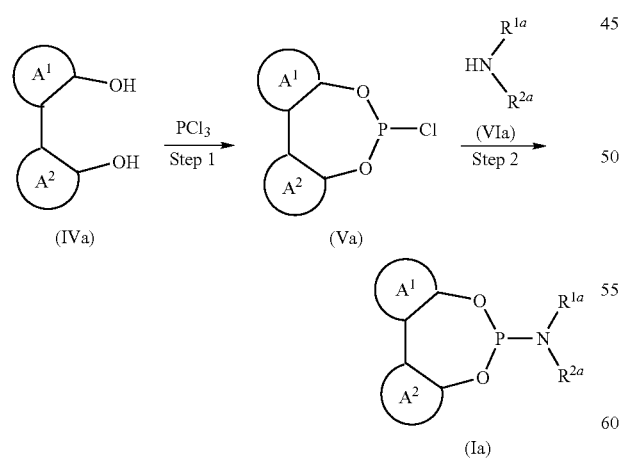

wherein each symbol is as defined above.

The amount of the phosphorus trichloride to be used for the reaction of Step 1 is generally 5 to 30 mol, preferably 10 to 20 mol, per 1 mol of diol (IVa).

The reaction is preferably carried out in the presence of a catalytic amount of a base such as N-methylpyrrolidone, N,N-dimethylformamide and the like.

The reaction is carried out without a solvent or in a solvent inert to the reaction, preferably without a solvent, from the aspects of reactivity. Examples of the solvent to be used include halogenated solvents such as dichlorobenzene and the like, and the like.

The reaction is carried out by mixing diol (IVa), phosphorus trichloride and a catalytic amount of the base.

The reaction temperature is generally 20 to 80° C., preferably 30 to 70° C. While the reaction time varies depending on the kind of diol (IVa) to be used, it is generally 5 min to 6 hr, preferably 15 min to 3 hr.

After completion of the reaction, an excess amount of the phosphorus trichloride can be removed by azeotroping the reaction mixture with toluene, chlorobenzene and the like. The obtained phosphorcholoridite (Va) may be used for the next step without purification.

The amount of amine (VIa) to be used for the reaction of Step 2 is generally 1 to 2 mol, preferably 1.1 to 1.5 mol, per 1 mol of diol (IVa).

The reaction is preferably carried out in the presence of a base such as n-butyllithium, lithiumdiisopropylamide and the like. The amount of the base to be used is generally 1 to 2 mol, preferably 1 to 1.5 mol, per 1 mol of amine (VIa).

The reaction is preferably in a solvent inert to the reaction. Examples of the solvent include ether solvents such as tetrahydrofuran, methyl tert-butyl ether and the like, and the like.

The reaction is carried out by adding a base to amine (VIa) in a solvent, and then adding phosphorcholoridite (Va) thereto.

The reaction temperature is generally −80 to 30° C. While the reaction time varies depending on the kind of phosphorcholoridite (Va) and amine (VIa) to be used, it is generally 1 to 12 hr.

After completion of the reaction, phosphoramidite ligand (Ia) is obtained by conventional workup such as separating operation, concentration and the like. Where necessary, it may be purified by an operation such as recrystallization, column chromatography and the like.

EXAMPLE

The present invention is explained in detail in the following by referring to Examples, which are not to be construed as limitative.

Example 1

Synthesis of (3,5-dioxa-4-phospha-cyclohepta[2,1-a;3,4-a']diphenyl-4-en)-dibenzo[b,f]azepine

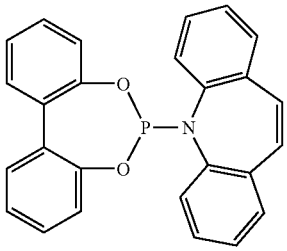

A Schlenk flask under argon was charged with 2,2'-biphenol (2.23 g, 12.0 mmol, 1 eq.), phosphorus trichloride (24.7 g, 180 mmol, 15 eq.) and a catalytic amount of N-methylpyrrolidone (35.7 mg, 0.36 mmol, 0.03 eq.) were added, and the reaction mixture was heated at 50° C. for 30 min. The initially heterogeneous mixture turned into a brownish homogenous solution. After cooling to 23° C., the excess phosphorus trichloride was evaporated in vacuo, and toluene (1 mL) was added to azeotropically remove the remaining phosphorus trichloride. The resulting phosphorchloridite was redissolved in THF (25 mL).

In a separate Schlenk flask under argon, dibenzo[b,f] azepine (2.78 g, 14.4 mmol, 1.2 eq.) dissolved in THF (25 mL) was deprotonated at −78° C. by the slow addition of n-butyllithium (1.1 eq., 1.6 M solution in hexanes). The resulting deep blue solution was continued to stir at −78° C. for 1 hr before the phosphorchloridite solution obtained above was slowly transferred via cannula. The resulting mixture was stirred at −78° C., and then warmed to 23° C. and continued to stir for 8 hr. After completion of the reaction, as determined by TLC, the solvent was evaporated in vacuo. Purification of the residue by flash chromatography on silica gel using hexanes/toluene as an eluent afforded the title compound (1.35 g, 3.31 mmol, yield 28%, off-white powder) as a white foam.

mp 159° C.

IR (neat) ν 3062, 3025, 1486, 1434, 1196, 1095, 984, 890, 848, 759, 746

$^1$H-NMR (300 MHz, CDCl$_3$) δ: 7.35-7.38 (m, 2H), 7.22-7.27 (m, 4H), 7.10-7.20 (m, 8H), 6.98-7.08 (m, 2H), 6.96 (s, 2H)

$^{13}$C-NMR (75 MHz, CDCl$_3$) δ: 150.6, 142.4, 135.8, 131.3, 130.4, 130.3, 129.4, 128.9, 128.8, 128.7, 126.4, 124.2, 121.9

$^{31}$P-NMR (121 MHz, CDCl$_3$) 137.9

HR-MALDI-MS m/z calcd for $C_{26}H_{18}NO_2P$ [M+H]+ 408.1148, found 408.1149

Example 2

Synthesis of (3,5-dioxa-4-phospha-cyclohepta[2,1-a; 3,4-a']diphenyl-4-en)-10,11-dihydro-dibenzo[b,f] azepine

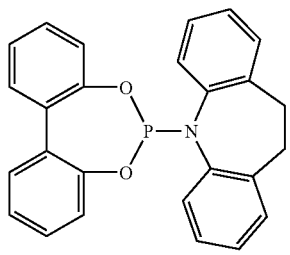

In the same manner as in Example 1 and using 2,2'-biphenol (834 mg, 4.48 mmol) and, instead of dibenzo[b,f]azepine, dihydrodibenzo[b,f]azepine (1.05 g, 5.37 mmol, 1.2 eq.), the title compound was synthesized (568 mg, 1.39=mol, yield 31%, off-white powder).

mp 145° C.

IR (neat) ν 3061, 3029, 1486, 1436, 1184, 1094, 990, 880, 842, 699

$^1$H-NMR (300 MHz, CDCl$_3$) δ: 7.43-6.94 (m, 16H), 3.77-3.61 (m, 2H), 3.01-2.93 (m, 2H)

$^{13}$C-NMR (75 MHz, CDCl$_3$) δ: 150.5, 142.3, 136.8, 130.2, 130.0, 129.9, 128.8, 127.9, 126.5, 126.2, 124.2, 121.2, 31.6

$^{31}$P-NMR (121 MHz, CDCl$_3$) 136.4

HR-MALDI-MS m/z calcd for $C_{26}H_{20}NO_2P$ [M+H]+ 410.1304, found 410.1303

Example 3

Synthesis of (S)-(+)-(3,5-dioxa-4-phospha-cyclohepta[2,1-a; 3,4-a']dinaphthalen-4-yl)-dibenzo[b,f]-azepine

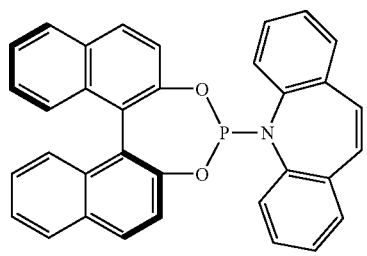

In the same manner as in Example 1 and using (S)-BINOL (300 mg, 1.05 mmol) instead of 2,2'-biphenol, the title compound was synthesized (239 mg, 0.47 mmol, yield 45%, off-white powder).

mp 246° C.

$[\alpha]_D^{25}$+313.6 (c 1.07, CHCl$_3$)

IR (neat) ν 3057, 3023, 1590, 1484, 1236, 1201, 1070, 979, 938, 800, 767

$^1$H-NMR (500 MHz, CDCl$_3$) δ: 7.96 (d, J=8.8 Hz, 1H), 7.87 (d, J=8.2 Hz, 1H), 7.73 (d, J=8.1 Hz, 1H), 7.60 (dd, J=8.8, 0.7 Hz, 1H), 7.41 (d, J=8.7 Hz, 1H), 7.38-7.31 (m, 2H), 7.23-7.13 (m, 2H), 7.19-7.13 (m, 6H), 7.11-7.07 (m, 1H), 6.96 (d, J=11.6 Hz, 1H), 6.92-6.87 (m, 2H), 6.84 (dd, J=8.8, 0.5 Hz, 1H), 6.53-6.49 (m, 2H)

$^{13}$C-NMR (125 MHz, CDCl$_3$) δ: 149.9, 149.9, 148.7, 143.0, 142.8, 142.5, 135.4, 135.2, 132.8, 132.1, 131.5, 131.4, 131.3, 130.2, 130.1, 129.1, 129.0, 128.9, 128.8, 128.5, 128.4, 128.3, 128.3, 127.8, 126.8, 126.7, 126.1, 126.0, 125.6, 124.8, 124.2, 122.1, 121.5, 121.1

$^{31}$P-NMR (121 MHz, CDCl$_3$) 138.0

HR-MALDI-MS m/z calcd for $C_{34}H_{22}NO_2P$ [M+H]+ 508.1461, found 508.1463

Example 4

Synthesis of 5-phenylpent-1-en-3-amine hydrochloride

A Schlenk flask under argon was charged with {Ir(cod)Cl}$_2$ (10 mg, 15 mmol, 1.5 mol %) and ligand (3,5-dioxa-4-phospha-cyclohepta[2,1-a; 3,4-a']diphenyl-4-en)-dibenzo[b,f]azepine (12 mg, 30 μmol, 3 mol %). N,N-Dimethylformamide (2 mL) was added and the reaction mixture was stirred at 23° C. for 15 min. 5-Phenylpent-1-en-3-ol (1.00 mmol, 1 eq.) was added via syringe followed by the addition of solid sulfamic acid (97 mg, 1.00 mmol, 1 eq.). The resulting reaction mixture was heated to 50° C. After completion of the reaction (usually 6-7 hr), as determined by TLC, the solvent was evaporated at high vacuum. The resulting brown residue was dissolved in methylene chloride (10 mL) and saturated aqueous sodium hydrogencarbonate solution (10 mL), and the mixture was stirred for 10 min. The aqueous layer was extracted with methylene chloride (3×15 mL). The combined organic layers were dried (sodium sulfate) and concentrated under reduced pressure. The ratio of regioisomers was determined by $^1$H-NMR analysis of the unpurified sample. Purification of the residue by flash chromatography on basic or neutral alumina using methylene chloride/methanol as an eluent afforded the desired amine. They were precipitated by addition of 2M hydrochloric acid in diethyl ether to give the title compound (162 mg, 0.82 mmol, yield 82%).

mp 168° C.;

IR (neat) ν 2882(br), 2045, 1601, 1511, 1453, 988, 936, 765, 745

$^1$H-NMR (300 MHz, CDCl$_3$) δ: 8.67 (br.s, 3H), 7.31-7.19 (m, 5H), 5.93 (ddd, J=17.3, 10.5, 7.7 Hz, 1H), 5.47 (d, J=17.3 Hz, 1H), 5.36 (d, J=10.5 Hz), 3.74 (br.s, 1H), 2.82-2.64 (m, 2H), 2.32-2.04 (m, 2H)

$^{13}$C-NMR (75 MHz, CDCl$_3$) δ: 139.8, 132.9, 128.4, 128.3, 126.2, 121.2, 54.1, 34.7, 31.4

HR-ESI-MS m/z calcd for $C_{11}H_{13}[M-NH_3]^+$ 145.1012, found 145.1012

Combustion analysis: calcd for $C_{11}H_{16}NCl$: C, 66.83; H, 8.16; N, 7.08. found C, 66.54; H, 8.09; N, 6.81.

Example 5

Synthesis of N-(5-phenylpent-1-en-3-yl)benzamide

A Schlenk flask under argon was charged with {Ir(cod)Cl}$_2$ (10 mg, 15 μmol, 3 mol %) and ligand (3,5-dioxa-4-phospha-cyclohepta[2,1-a; 3,4-a']diphenyl-4-en)-dibenzo[b,f]azepine (12 mg, 30 μmol, 6 mol %). N,N-Dimethylformamide (2 mL) was added and the reaction mixture was stirred at 23° C. for 15 min. 5-Phenylpent-1-en-3-ol (81 mg, 0.50 mmol, 1 eq.) was added via syringe followed by the addition of solid sulfamic acid (49 mg, 0.50 mmol, 1 eq.). The resulting reaction mixture was heated to 50° C. Conversion was checked by disappearance of the starting material on TLC and/or by measuring $^1$H-NMR of an aliquot taken from the reaction mixture. After completion of the reaction (usually 3-4 hr), triethylamine (202 mg, 2.00 mmol, 4 eq.) and freshly distilled benzoyl chloride (141 mg, 1.00 mmol, 2 eq.) were added to the reaction mixture and the mixture was stirred for 4 hr at 23° C. Subsequently, the reaction mixture was partitioned between methylene chloride (10 mL) and water (10 mL). The aqueous layer was extracted with methylene chloride (3×15 mL). The combined organic layers were dried (sodium sulfate) and concentrated under reduced pressure. Purification of the residue by flash chromatography on silica gel using hexanes/ethyl acetate as an eluent afforded the title compound (97 mg, 0.37 mmol, yield 73%) as an off-white solid.

mp 131° C.;

IR (neat) ν 3326, 2946, 2979, 2862, 1633, 1526, 1487, 1334, 1292, 920, 748, 698

$^1$H-NMR (300 MHz, CDCl$_3$) δ: 7.71-7.68 (m, 2H), 7.52-7.37 (m, 3H), 7.31-7.17 (m, 5H), 6.11 (d, J=8.2 Hz, 1H), 5.90 (ddd, J=17.2, 10.4, 5.6 Hz, 1H), 5.24 (dd, J=17.2, 1.2 Hz, 1H), 5.18 (dd, J=10.4, 1.2 Hz, 1H), 4.76 (br. quintet, 1H), 2.75 (t, J=2.9 Hz, 2H), 2.10-1.90 (m, 2H)

$^{13}$C-NMR (75 MHz, CDCl$_3$) δ: 166.7, 141.5, 138.0, 134.5, 131.4, 128.5, 128.4, 128.4, 126.8, 126.0, 115.4, 51.6, 36.3, 32.1

HR-MALDI-MS m/z calcd for $C_{18}H_{19}NO$ $[M+H]^+$ 266.1539, found 266.1538

Example 6

Synthesis of tert-butyl 5-phenylpent-1-en-3-ylcarbamate

A Schlenk flask under argon was charged with {Ir(cod)Cl}$_2$ (10 mg, 15 μmol, 3 mol %) and ligand (3,5-dioxa-4-phospha-cyclohepta[2,1-a; 3,4-a']diphenyl-4-en)-dibenzo[b,f]azepine (12 mg, 30 μmol, 6 mol %). N,N-Dimethylformamide (2 mL) was added and the reaction mixture was stirred at 23° C. for 15 min. 5-Phenylpent-1-en-3-ol (81 mg, 0.50 mmol, 1 eq.) was added via syringe followed by the addition of solid sulfamic acid (49 mg, 0.50 mmol, 1 eq.). The resulting reaction mixture was heated to 50° C. Conversion was checked by disappearance of the starting material on TLC and/or by measuring $^1$H-NMR of an aliquot taken from the reaction mixture. After completion of the reaction (usually 3-4 hr), the reaction mixture was carefully concentrated and cooled to 23° C. The resulting brownish oil was redissolved in methylene chloride (3 mL), and Boc$_2$O (202 mg, 1.00 mmol, 2 eq.) and a catalytic amount (ca. 10 mg) of the phase-transfer reagent n-Bu$_4$NHSO$_4$ were added at 0° C. At 0° C., the reaction mixture was treated with 0.5 M aqueous sodium hydroxide solution (3 mL) and warmed to 23° C. for 6 hr. Subsequently, the reaction mixture was partitioned between methylene chloride (10 mL) and water (10 mL). The aqueous layer was extracted with methylene chloride (3×15 mL). The combined organic layers were dried (sodium sulfate) and concentrated under reduced pressure. Purification of the residue by flash chromatography on silica gel using hexanes/ethyl acetate as an eluent afforded the title compound (93 mg, 0.36 mmol, yield 71%) as an off-white solid.

mp 53° C.

IR (neat) ν 3364, 3028, 2979, 2945, 1681, 1517, 1330, 1243, 1172, 1045, 1030, 926, 752, 701

$^1$H-NMR (300 MHz, CDCl$_3$) δ: 7.17-7.31 (m, 5H), 5.79 (ddd, J=16.5, 10.3, 5.6 Hz, 1H), 5.10-5.21 (m, 2H), 4.49 (br.s, 1H), 4.16 (br.s, 1H), 2.62-2.96 (m, 2H), 1.78-1.89 (m, 2H), 1.46 (s, 9H)

$^{13}$C-NMR (75 MHz, CDCl$_3$) δ: 155.2, 141.5, 138.6, 128.3, 128.2, 125.8, 114.6, 79.3, 52.6, 37.0, 32.2, 28.6

HR-ESI-MS m/z calcd for $C_{16}H_{23}NO_2Na$ $[MNa]^+$ 284.1621, found 284.1623

Example 7

Synthesis of 2,2,2-trifluoro-N-(5-phenylpent-1-en-3-yl)acetamide

A Schlenk flask under argon was charged with {Ir(cod)Cl}$_2$ (10 mg, 15 μmol, 3 mol %) and ligand (3,5-dioxa-4-phospha-cyclohepta[2,1-a; 3,4-a']diphenyl-4-en)-dibenzo[b,f]azepine (12 mg, 30 μmol, 6 mol %). N,N-Dimethylformamide (2 mL) was added and the reaction mixture was stirred at 23° C. for 15 min. 5-Phenylpent-1-en-3-ol (81 mg, 0.50 mmol, 1 eq.) was added via syringe followed by the addition of solid sulfamic acid (49 mg, 0.50 mmol, 1 eq.). The resulting reaction mixture was heated to 50° C. Conversion was checked by disappearance of the starting material on TLC and/or by measuring $^1$H-NMR of an aliquot taken from the reaction mixture. After completion of the reaction (usually 3-4 hr), the reaction mixture was carefully concentrated and cooled to 23° C. The resulting brownish oil was redissolved in methylene chloride (2 mL), and trifluoroacetic anhydride (315 mg, 1.50 mmol, 3 eq.) and anhydrous potassium carbonate (solid, 276 mg, 2.00 mmol, 4 equiv) were added at 0° C. The reaction mixture was continued to stir for 8 hr at 23° C. Subsequently, it was partitioned between methylene chloride (10 mL) and water (10 mL). The aqueous layer was extracted with methylene chloride (3×15 mL). The combined organic layers were dried (sodium sulfate) and concentrated under reduced pressure. Purification of the residue by flash chromatography on silica gel using hexanes/ethyl acetate as an eluent afforded the title compound (91 mg, 0.36 mmol, yield 71%) as a yellow oil.

IR (neat) ν 3293, 3088, 2928, 1698, 1554, 1206, 1181, 1154, 747, 724, 698

$^1$H-NMR (300 MHz, CDCl$_3$) δ: 7.13-7.99 (m, 5H), 6.14 (br.s, 1H), 5.79 (ddd, J=17.0, 10.7, 6.0 Hz, 1H), 5.19-5.25 (m, 2H), 4.46-4.55 (br.quintet, 1H), 2.67 (t, J=7.8 Hz, 2H), 1.89-2.01 (m, 2H)

$^{13}$C-NMR (75 MHz, CDCl$_3$) δ: 156.5 (q, J=36.9 Hz), 140.6, 135.9, 128.6, 128.3, 126.3, 117.0, 115.8 (q, J=288.3 Hz), 52.1, 35.7, 31.9

$^{19}$F-NMR (282 MHz, CDCl$_3$) −75.7

HR-ESI-MS m/z calcd for C$_{13}$H$_{14}$NOF$_3$Na [MNa]$^+$ 280.0919, found 280.0919

Example 8

Synthesis of 1-phenylprop-2-en-1-amine hydrochloride

In the same manner as in Example 4, the title compound was synthesized (132 mg, 0.78 mmol, yield 78%) as an off-white solid.

$^1$H-NMR (300 MHz, CD$_3$OD) δ: 7.43-7.57 (m, 5H), 6.19 (ddd, J=17.3, 10.6, 6.5 Hz, 1H), 5.51 (dd, J=10.6, 1.0 Hz, 1H), 5.44 (dd, J=17.3, 1.3 Hz, 1H), 5.04 (d, J=6.5 Hz, 1H), 4.55 (br.s, 3H)

Example 9

Synthesis of 1-cyclohexylprop-2-en-1-amine hydrochloride

In the same manner as in Example 4, the title compound was synthesized (132 mg, 0.75 mmol, yield 75%) as white flakes.

mp 231° C.

IR (neat) ν 3274, 2921, 2851, 1629, 1600, 1510, 1447, 993, 933, 918, 687

$^1$H-NMR (300 MHz, CDCl$_3$) δ: 8.54 (br.s, 3H), 5.91-5.79 (ddd, J=17.3, 9.6, 6.9 Hz, 1H), 5.42 (d, J=17.3 Hz, 1H), 5.37 (d, J=9.6 Hz, 1H) 3.51-3.46 (m, 1H), 1.89-1.61 (m, 6H), 1.45-1.03 (m, 5H)

$^{13}$C-NMR (75 MHz, CDCl$_3$) δ: 131.9, 121.0, 59.5, 40.3, 29.1, 28.1, 25.6

HR-ESI-MS m/z calcd for C$_{11}$H$_{13}$[MH—NH$_3$]$^+$ 145.1012, found 145.1012

Example 10

Synthesis of 1-(benzyloxy)but-3-en-2-amine hydrochloride

In the same manner as in Example 4, the title compound was synthesized (152 mg, 0.71 mmol, yield 71%) as a white powder.

$^1$H-NMR (300 MHz, CD$_3$OD) δ: 7.39-7.26 (m, 5H), 5.88 (m, 1H), 5.41 (d, J=17.4 Hz, 1H), 5.37 (d, J=11.2 Hz, 1H), 4.59 (s, 2H), 3.87 (m, 1H), 3.64 (dd, J=10.1, 3.9 Hz, 1H), 3.49 (dd, J=10.1, 7.8 Hz, 1H).

Example 11

Synthesis of hexa-1,5-dien-3-amine hydrochloride

In the same manner as in Example 4, the title compound was synthesized (101 mg, 0.75 mmol, yield 75%) as an off-white solid. Isomerization of double bond was not observed.

$^1$H-NMR (300 MHz, D$_2$O) δ: 5.64-5.86 (m, 2H), 5.14-5.34 (m, 4H), 3.81 (q, J=6.7 Hz, 1H), 2.31-2.46 (m, 2H).

Example 12

Synthesis of (S)-1-cyclohexylprop-2-en-1-amine hydrochloride

A Schlenk flask under argon was charged with {IrCl$_2$(coe)$_2$}$_2$ (13.1 mg, 15 μmol, 3 mol %) and ligand (S)-(+)-(3,5-dioxa-4-phospha-cyclohepta[2,1-a; 3,4-a']dinaphthalen-4-yl)-dibenzo[b,f]-azepine (16.2 mg, 30 μmol, 6 mol %). N,N-Dimethylformamide (2 mL) was added and the reaction mixture was stirred at 23° C. for 15 min. Racemic 1-cyclohexylprop-2-en-1-ol (70 mg, 0.50 mmol, 1 eq.) was added via syringe followed by the addition of solid sulfamic acid (49 mg, 0.50 mmol, 1 eq.). The resulting reaction mixture was stirred at 23° C. for 24 hr. After completion of the reaction, as determined by TLC, the solvent was carefully evaporated at high vacuum. The resulting brown residue was dissolved in methylene chloride (10 mL) and saturated aqueous sodium hydrogencarbonate solution (10 mL), and the mixture was stirred for 10 min. The aqueous layer was extracted with methylene chloride (3×15 mL). The combined organic layers were dried (sodium sulfate) and concentrated under reduced pressure. The ratio of regioisomers was determined by $^1$H-NMR analysis of the unpurified sample. Purification of the residue by flash chromatography on neutral alumina using methylene chloride/methanol as an eluent afforded the desired amine which was immediately treated with 2M hydrochloric acid in diethyl ether. The corresponding hydrochloride salt (the title compound, 61 mg, 0.35 mmol, yield 70%) precipitated as a white solid.

To determine the absolute configuration, the obtained amine hydrochloride (50 mg, 0.28 mmol, 1 eq.) was suspended in diethyl ether (1 mL) and treated with 6 M potassium hydroxide (0.5 mL, 10 eq.). After stirring at 23° C. for 30 min, the mixture was partitioned between diethyl ether and water. The aqueous phase was extracted three times with diethyl ether. The combined organic layers were washed with brine and dried over magnesium sulfate. The mixture was carefully concentrated under reduced pressure to obtain a brownish oil that was immediately dissolved in methylene chloride (2 mL) and treated with triethylamine (115 mg, 1.14 mmol, 4 eq.) and freshly distilled trichloroacetyl chloride (103 mg, 0.57 mmol, 2 eq.). After 3 hr stirring at 23° C., the reaction mixture was partitioned between methylene chloride and water. The aqueous phase was extracted three times with methylene chloride. The combined organic layers were washed with brine and dried over magnesium sulfate. Concentration of the mixture under reduced pressure yielded in a brownish residue that was subjected to chromatography on silica gel (30:1 hexanes/ethyl acetate) to give 2,2,2-trichloro-N-(1-cyclohexylallyl)acetamide (36 mg, 0.13 mmol, 45%) as a colorless solid. The optical rotation was measured: $[\alpha]_D^{25}$−26.5 (c 0.45, CHCl$_3$);

Comparison to the literature $[\alpha]_D^{25}$+30.7 (c 0.42, CHCl$_3$) (C. E. Anderson, L. E. Overman, J. Am. Chem. Soc. 2003, 125, 12412-12413) allowed to establish the absolute configuration for the product as: (S)-2,2,2-Trichloro-N-(1-cyclohexylallyl) acetamide.

$^1$H-NMR (300 MHz, CDCl$_3$) δ 6.58 (brs, 1H), 5.79 (ddd, J=17.1, 10.5, 6.0 Hz, 1H), 5.19-5.25 (m, 2H), 4.27 (dd, J=14.8, 6.2 Hz, 1H), 1.65-1.81 (m, 5H), 1.51-1.60 (m, 1H), 0.95-1.30 (m, 5H)

According to the present invention, a primary allylic amine can be produced directly from an allylic alcohol, without conventional use of an activator for an allylic alcohol and conversion of an allylic alcohol into an activated compound thereof.

This application is based on patent application No. 216396/2007 filed in Japan, the contents of which are hereby incorporated by reference.

The invention claimed is:

1. A phosphoramidite ligand represented by the formula (Ia):

(Ia)

wherein
ring A$^1$ and ring A$^2$ are the same or different and each is an aromatic hydrocarbon ring optionally having substituent(s), and
R$^{1a}$ and R$^{2a}$ form, together with the nitrogen atom they are bonded to, wherein
------ is a single bond or a double bond, which optionally has substituent(s).

2. The phosphoramidite ligand of claim 1, wherein R$^{1a}$ and R$^{2a}$ form, together with the nitrogen atom they are bonded to, which optionally has substituent(s).

3. The phosphoramidite ligand of claim 1, wherein ring A$^1$ and ring A$^2$ are the same or different and each is a benzene ring optionally having substituent(s) or a naphthalene ring optionally having substituent(s).

4. The phosphoramidite ligand of claim 1, wherein ring A$^1$ and ring A$^2$ are both benzene rings optionally having substituent(s) or both naphthalene rings optionally having substituent(s).

5. The phosphoramidite ligand of claim 1, which is or

.

6. The phosphoramidite ligand of claim 1, which is a chiral ligand.

7. The phosphoramidite ligand of claim 1, which is or

.

8. A catalyst comprising the phosphoramidite ligand of claim 1 and an iridium complex.

9. The catalyst of claim 8, wherein the iridium complex is {Ir(1,5-cyclooctadiene)Cl}$_2$ or {IrCl(cyclooctene)$_2$}$_2$.

* * * * *